US006271196B1

(12) United States Patent
O'Brien

(10) Patent No.: US 6,271,196 B1
(45) Date of Patent: *Aug. 7, 2001

(54) METHODS OF ALLEVIATING NEUROPATHIC PAIN USING PROSAPOSIN-DERIVED PEPTIDES

(75) Inventor: John S. O'Brien, San Diego, CA (US)

(73) Assignee: Regents of the University of CA, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/611,307

(22) Filed: Mar. 5, 1996

(51) Int. Cl.[7] .......................... A61K 38/17; A61K 38/10

(52) U.S. Cl. .................... 514/2; 514/13; 514/14
(58) Field of Search ...................... 514/2, 13, 14

(56) References Cited

U.S. PATENT DOCUMENTS

| 5,470,582 | 11/1995 | Supersaxo et al. | 424/489 |
| 5,571,787 | 11/1996 | O'Brien et al. | 514/12 |

FOREIGN PATENT DOCUMENTS

0246753 A2   11/1987   (EP) .

OTHER PUBLICATIONS

Hong et al., Intercellular Adhesion Molecule–1 Expression Induced by Interleukin (IL)–1B or IL–1B Fragment is blocked by an IL–1 Receptor Antagonist and a Soluble IL–1 Receptor, Journal of Neuroimmunology 44(2):163–170 (Jun. 1993).
Jackowski, Neural Injury Repair: Hope for the Future as Barriers to Effective CNS Regeneration Become Clearer., British Journal of Neurosurgery 9:303–317.
Kotani et al., Prosaposin Facilitates Sciatic Nerve Regeneration In Vivo, Journal of Neurochemistry 66(5):2019–2025 (May 1996).
McMahon, Stephen B. et al., Peripheral neuropathies and neurotrophic facts: animal modes and clinical perspectives, *Current Opinion in Neurobiology* (1995) 5:616–624.
Kotani, Ytasurori, et al., "A Hydrophilic Peptide Comprising 18 Amino Acid Residues of the Prosaposin Sequence Has Neurotrophic Activity In Vitro and In Vivo", *J. Neurochemistry*, (May 1966) 66(5):2197–2200.
Bennett, "Neuropathic Pain", *Textbook of Pain* pp201–224, (1994).
Bonica & Butler, "Local Anesthesia and regional blocks" *Textbook of Pain* pp. 997–1023 (1994).
Botney & Fields, "Amitriptyline Potentiates Morphine Analgesia by a Direct Action on the Central Nervous System" *Ann. Neurol.* 13(2):160–164, (1983).

Calcutt et al., "Different effect of two aldose reductase inhibitors on nociception and prostaglandin E" *Eur. J. Pharmacol.* 285: 189–197, (1995).
Calcutt et al., "Tactile allodynia and formalin hyperalgesia in streptozotocin–diabetic rats: effects of insulin, aldose reductase inhibition and lidocaine" *Pain* 68:293–299 (1996).
Calcutt et al. "Tolrestat treatment prevents modification of the formalin test model of prolonged pain in hyperglycemic rats", *Pain* 58:413–420, (1994).
Campana et al., "Induction of MAPK Phosphorylation by Prosaposin and Prosaptide in PC12 Cells" *Biochem. Biophys. Res. Comm.* 229(3):706–712, (1996).
Choi et al., "Behavioral Signs of Ongoing Pain and Cold Allodynia in a Rat Model of Neuropathic Pain" *Pain* 59: 369–376, (1994).
Devor, "The pathophysiology of damaged peripheal nerves" *Textbook of Pain,* pp. 79–100, (1994).
France, "Chronic Pain and Depression", *J. Pain Symptom Manage* 2(4):234–236 (1987).
Galbraith et al. "A System to measure Thermal Nociception", *J. Neurosci. Meth.* 49:63–68, (1993).
Karagiannis et al., "Synthesis of a potent antagonist of substance P by Replacing the $CH_2SCH_3$ and the $\alpha$–carboxamide groups of the methionine at [$Orn^{6}$–$SP^{6-11}$by benzyl ester groups", *Int. J. Peptide Protein Res.* 42:565–569 (1993).
Kishore–Kumar et al., "Desipramine relieves postherpetic neuralgia" *Clin. Pharmacol. Ther.* 47(3):305–312, (1990).
Manolopoulou et al., "Synthesis of potent antagonists of substance P by modifying the methionyl and glutaminyl residues of its C–terminal hexapeptide and without using D–amino acids", Int. J. Peptide Protein Res.41: 411–414 (1993).
Malik and Calcutt "Diabetic Neuropathy", *Anesthesia: Biologic Foundations,* Eds., pp. 869–877, (1997).
Max et al., " Amitriptyline relives diabetic neuropathy pain in patients with normal or depressed mood", *Neurology* 37(4):589–596, (1987).
Max et al., "Amitriptyline, but not Lorazepam, relieves postherpetic neuralgia", *Neurology* 38(9):1427–1432, (1988).
Meyer et al. "Peripheral neural mechanisms of nociception" *Textbook of Pain,* pp13–44, 1994.
Myers (*NIH Workshop on Low Back Pain,* Eds., J. Weinstein, S. Gordon, American Academy of Orthopaedic Surgeons, 1995).

(List continued on next page.)

Primary Examiner—Patricia A. Duffy
Assistant Examiner—Robert C. Hayes
(74) Attorney, Agent, or Firm—Fuess & Davidenas

(57) ABSTRACT

The invention provides a method of alleviating neuropathic pain in a subject by administering an effective amount of an active fragment of prosaposin to the subject. The invention also provides a method of preventing neuropathic pain in a subject by administering an effective amount of an active fragment of prosaposin to the subject.

7 Claims, 2 Drawing Sheets

OTHER PUBLICATIONS

Seltzer et al., "A novel behavioral model of neuropathic pain disorders produced in rats by partial sciatic nerve injury", *Pain 43:*205–218, (1990).

Shir & Seltzer, " A–fibers mediate mechanical hyperesthesia and allodynia and C–fibers mediate thermal hyperalgesia in a new model of causalgiform pain disorders in rats", *Neurosci. Lett. 115:*62–67 (1990).

Spiegel et al., " Analgesic Activity of Tricyclic Antidepressants", *Ann Neurol. 13*(4):462–465, (1983).

Triguero et al., "Capillary Depletion Method for Quantification of Blood–Brain Carrier Transport of Circulating peptides and Plasma Proteins", *J. Neurochemistry* 54(6):1882–1888 (Jun. 1990).

Ventafridda et al. Pain 43(2): 155–162, ( 1990).

Wagner & Myers, "Endoneurial injection of TNF–α produces neuropathic pain behaviors", *NeuroReport* 7:2897–2901 (1996).

Yaksh in "Preclinical Models of Nociception", Anesthesia: Biologic Foundations, Eds., Yaksh et al. Lippincot–Raven, pp. 869–877, 1997.

Bennett, "An Animal Model of Neuropathic Pain: A Review," *Muscle & Nerve* 16:1040–1048 (1993).

Campana et al., "Prosaptide, a Peptide Derived From Prosaposin, Induces Motor Endplate Sprouting and Prevents Taxol Neuropathy," *Society for Neurosciences* 21:554 (1995).

Kim and Chung, "An Experimental Model for Peripheral Neuropathy Produced by Segmental Spinal Nerve Ligation in the Rat," *Pain,* 50:355–363 (1992).

Myers, "The Pathogenesis of Neuropathic Pain," *Regional Anesthesia* 20(3):173–184 (1995).

O'Brien et al., "Identification of Prosaposin as a Neurotrophic Factor," *Proc. Natl. Acad. Sci. USA* 91:9593–9596 (1994).

O'Brien and Kishimoto, "Saposin Proteins: Structure, Function, and Role in Human Lysosomal Storage Disorders," *FASEB J.* 5:301–308 (1991).

O'Brien et al., "Identification of the Neurotrophic Factor Sequence of Prosaposin," *FASEB J.* 9:681–685 (1995).

Sano et al., "Protection by Prosaposin Against Ischemia–Induced Learning Disability and Neuronal Loss," *Biochem. Biophys. Res. Commun.* 204(2):994–1000 (1994).

Hefti et al. Neurobiol. of Aging 9 (1988) 689–690.*

Rudinger et al. In "Peptide Hormones" (Jun. 1976) ed. J.A. Parsons, University Park Press, Baltimore, p. 1–7.*

The Merck Manual, sixteenth edition (1992), ed. Robert Berkow, Merck Research Laboratories, Rathway NJ pp. 1416–1419.*

* cited by examiner

METHODS OF ALLEVIATING NEUROPATHIC PAIN USING PROSAPOSIN-DERIVED PEPTIDES

BACKGROUND OF THE INVENTION

1. Field of the Invention

This invention relates generally to the field of pain therapy and more specifically to the use of prosaposin-derived peptides for the treatment of neuropathic pain.

2. Background Information

Neuropathic pain results from injury to a nerve. In contrast to the immediate pain caused by tissue injury, neuropathic pain can develop days or months after a traumatic injury. Furthermore, while pain caused by tissue injury is usually limited in duration to the period of tissue repair, neuropathic pain frequently is long-lasting or chronic. Moreover, neuropathic pain can occur spontaneously or as a result of stimulation that normally is not painful.

The clinical causes of neuropathic pain are widespread and include both trauma and disease. For example, traumatic nerve compression or crush and traumatic injury to the brain or spinal cord are common causes of neuropathic pain. Furthermore, most traumatic nerve injuries also cause the formation of neuromas, in which pain occurs as a result of aberrant nerve regeneration. In addition, cancer-related neuropathic pain is caused when tumor growth painfully compresses adjacent nerves, brain or spinal cord. Neuropathic pain also is associated with diseases such as diabetes or alcoholism.

Unfortunately, neuropathic pain frequently is resistant to available drug therapies. In addition, current therapies have serious side-effects including, for example, cognitive changes, sedation, nausea and, in the case of narcotic drugs, addiction. Many patients suffering from neuropathic pain are elderly or have other medical conditions that particularly limit their tolerance of the side-effects associated with available drug therapy. The inadequacy of current therapy in relieving neuropathic pain without producing intolerable side-effects frequently is manifest in the depression and suicidal tendency of chronic pain sufferers.

Methods of alleviating neuropathic pain would improve the quality of life for many people suffering from pain due to trauma or disease. However, there currently are no effective drugs that relieve neuropathic pain without undesirable side-effects such as sedation and addiction. Thus, there is a need for methods of alleviating neuropathic pain without producing undesirable side-effects. The present invention satisfies this need and provides related advantages as well.

SUMMARY OF THE INVENTION

The present invention provides a method of alleviating neuropathic pain in a subject by administering an effective amount of an active fragment of prosaposin to the subject. For example, the invention provides a method of alleviating neuropathic pain resulting from a disorder of peripheral nerve, dorsal root ganglia, spinal cord, brainstem, thalamus or cortex in a subject by administering an effective amount of an active fragment of prosaposin having the amino acid sequence Cys-Glu-Phe-Leu-Val-Lys-Glu-Val-Thr-Lys-Leu-Ile-Asp-Asn-Asn-Lys-Thr-Glu-Lys-Glu-Ile-Leu (SEQ ID NO: 1) or Thr-D-Ala-Leu-Ile-Asp-Asn-Asn-Ala-Thr-Glu-Glu-Ile-Leu-Tyr (SEQ ID NO: 2). In addition, the invention provides a method of preventing neuropathic pain in a subject by administering an effective amount of an active fragment of prosaposin to the subject.

DETAILED DESCRIPTION OF THE INVENTION

Figure 1:
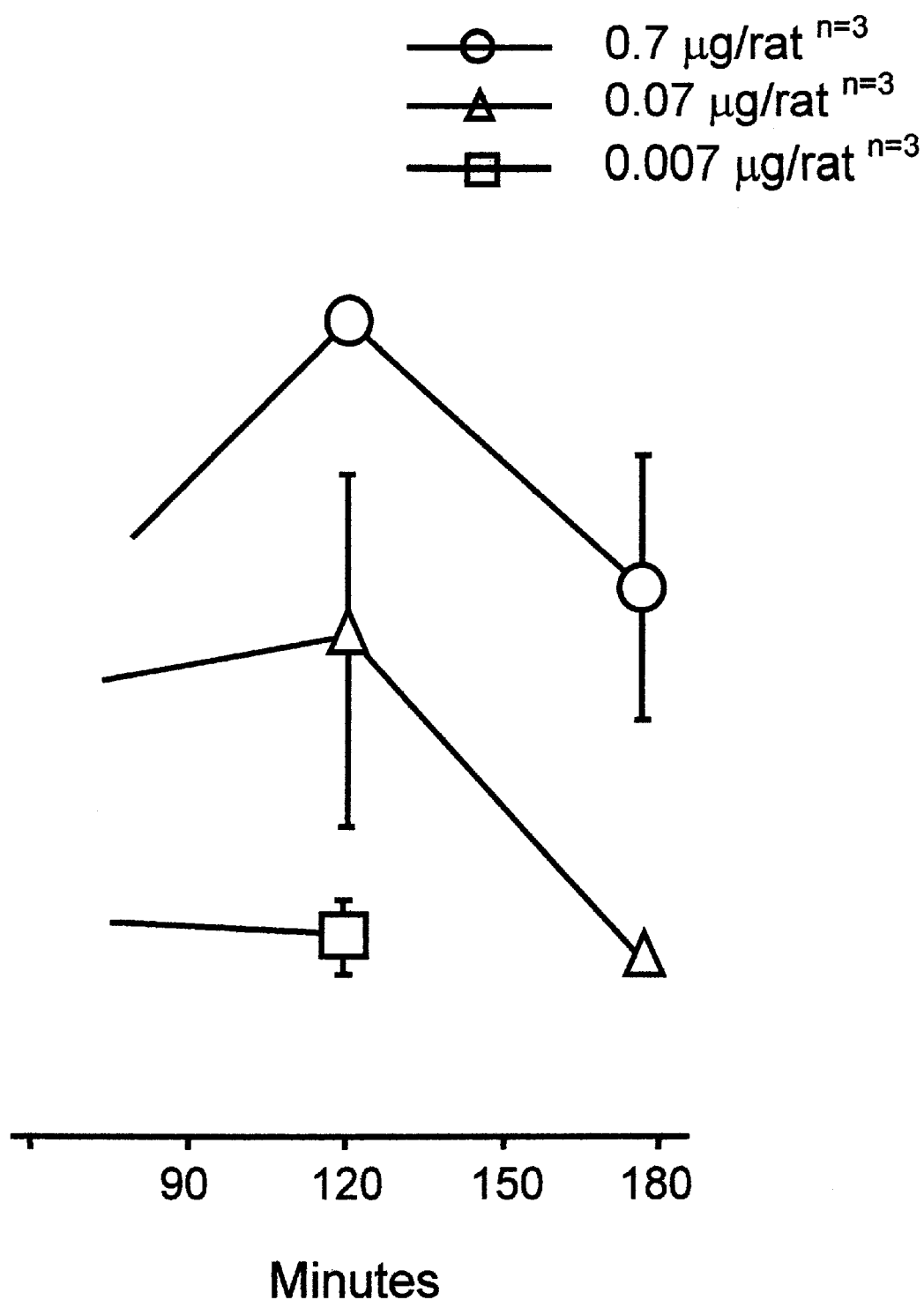
FIG. 1 shows the threshold of tactile allodynia before (time 0) and at various times after bolus injection of prosaposin-derived 22-mer peptide (SEQ ID NO: 1) in Chung model rats.

The present invention provides a method of alleviating neuropathic pain in a subject by administering an effective amount of an active fragment of prosaposin to the subject. As disclosed herein, the method of the invention can alleviate neuropathic pain in a subject within 30 minutes of administration. Such a method is useful for alleviating neuropathic pain resulting from a disorder of peripheral nerve, dorsal root ganglia, spinal cord, brainstem, thalamus or cortex.

A peptide useful in the invention is derived from prosaposin, which is a 517 amino acid protein originally identified as the precursor of four sphingolipid activator proteins (Kishimoto et al., *J. Lipid Res.*, 33:1255–1267 (1992)). Four adjacent tandem domains in prosaposin are proteolytically processed in lysosomes to generate saposins A, B, C, and D, which activate hydrolysis of glycospingolipids by lysosomal hydrolases (O'Brien and Kishimoto, *FASEB J.*, 5:301–308 (1991)).

The unprocessed form of prosaposin is found in high concentrations in human and rat brain, where it is localized within neuronal surface membranes. During embryonic development, prosaposin mRNA is abundant in brain and dorsal root ganglia. Furthermore, prosaposin binds with high affinity to gangliosides, which stimulate neurite outgrowth, and promotes transfer of gangliosides from micelles to membranes.

The neurotrophic activity of prosaposin is consistent with its localization in neuronal cell populations (O'Brien et al., *Proc. Natl. Acad. Sci. USA* 91:9593–9596 (1994); Sano et al., *Biochem. Biophys. Res. Commun.*, 204:994–1000 (1994), each of which is incorporated herein by reference). Prosaposin stimulates motor neurite outgrowth in vitro and in vivo and increases choline acetyltransferase activity, which is a marker of neuronal differentiation. In addition, prosaposin prevents cell death in neuroblastoma cells (O'Brien et al., supra, 1994; O'Brien et al., *FASEB J.* 9:681–685 (1995), which is incorporated herein by reference).

The neurotrophic activity of prosaposin is localized to saposin C, a domain of 80 amino acids. A 22-mer peptide corresponding to amino acids 8 to 29 of the saposin C domain (SEQ ID NO: 1) stimulates neurite outgrowth and choline acetyltransferase activity and prevents cell death in neuroblastoma cells (O'Brien et al., supra, 1995).

Prosaposin or the prosaposin-derived 22-mer peptide (SEQ ID NO: 1), for example, can modulate motor neuron function by promoting neurite outgrowth. Prior to the present invention, however, it was not known whether prosaposin or a peptide fragment of prosaposin could affect sensory neuron function. Moreover, the neurotrophic activity of prosaposin or a prosaposin-derived peptide in stimulating motor neurite outgrowth is evident only after a period of 24 to 48 hours (see, for example, O'Brien et al., supra, 1994). Neurotrophic activity of prosaposin or a prosaposin-derived peptide has not been demonstrated to occur in a shorter period of time.

In contrast, the present invention provides a method of alleviating neuropathic pain, which involves both sensory and motor neuron components. Furthermore, the method of the invention is effective in alleviating neuropathic pain in a matter of minutes rather than the hours or days previously demonstrated to be required for the neurotrophic activity of prosaposin or a prosaposin-derived peptide.

The effectiveness of the method of the invention in alleviating neuropathic pain was demonstrated using the well-recognized Chung rat model of peripheral neuropathy. In the Chung rat model, spinal nerve partial ligation of left spinal nerves L-5 and L-6 produces a long-lasting hypersensitivity to light pressure on the affected left foot. The hypersensitivity is similar to the pain experienced by humans with the neuropathic condition of causalgia (Kim and Chung, *Pain* 50:355–363 (1992), which is incorporated herein by reference).

Prior to administration of an active fragment of prosaposin, Chung model rats had a threshold of 3.0 to 4.0 g before the affected foot was withdrawn in response to pressure (Von Frey hairs) (see FIG. 1). After administration of an active fragment of prosaposin (prosaposin-derived 22-mer; SEQ ID NO: 1), neuropathic pain was alleviated, as evidenced by a greater tolerance to pressure before the affected foot was withdrawn. The effect of the active fragment of prosaposin occurred within 15 minutes and was sustained for 3 hours following administration as shown in FIG. 1. This rapid relief of neuropathic pain is in stark contrast to the delayed neurotrophic effects previously reported for prosaposin and peptides derived from prosaposin.

As used herein, the term "neuropathic pain" means pain resulting from injury to a nerve. Neuropathic pain is distinguished from nociceptive pain, which is the pain caused by acute tissue injury involving small cutaneous nerves or small nerves in muscle or connective tissue. Pain involving a nociceptive mechanism usually is limited in duration to the period of tissue repair and generally is alleviated by available analgesic agents or opioids (Myers, *Regional Anesthesia* 20:173–184 (1995), which is incorporated herein by reference).

Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Unlike nociceptive pain, neuropathic pain generally is resistant to opioid therapy (Myers, supra, 1995).

The method of the invention is useful in alleviating neuropathic pain resulting from a disorder of peripheral nerve, dorsal root ganglia, spinal cord, brainstem, thalamus or cortex. As used herein, the term "disorder" means any trauma, injury, disease or condition resulting in neuropathic pain.

The method of the invention is useful in alleviating neuropathic pain regardless of the etiology of the pain. For example, a method of the invention can be used to alleviate neuropathic pain resulting from a peripheral nerve disorder such as neuroma; nerve compression; nerve crush, nerve stretch or incomplete nerve transsection; mononeuropathy or polyneuropathy. A method of the invention also can be used to alleviate neuropathic pain resulting from a disorder such as dorsal root ganglion compression; inflammation of the spinal cord; contusion, tumor or hemisection of the spinal cord; tumors of the brainstem, thalamus or cortex; or trauma to the brainstem, thalamus or cortex (see, for example, Table 1).

The method of the invention can be useful, for example, to alleviate neuropathic pain resulting from a neuroma, which can develop readily after traumatic injury to nerve, especially when a whole nerve is severely crushed or transsected. In a neuroma, the neurite outgrowth that normally regenerates a peripheral nerve is aberrant or misguided due, for-example, to a physical obstruction such as scar tissue. Thus, a regenerating nerve fiber is entangled in an environment in which mechanical and physical factors precipitate abnormal electrophysiologic activity and pain (Myers, supra, 1995). An amputation neuroma, for example, can cause phantom pain or can cause pain triggered by the use of a limb prosthesis. As disclosed herein, such neuropathic pain can be alleviated by administration of an active fragment of prosaposin according to a method of the invention.

Nerve compression also results in neuropathic pain that can be treated using the method of the invention. Nerve compression can be abrupt, as in the case of traumatic nerve crush, or can be prolonged and moderate, secondary to tumor growth or scar formation in the proximity of a major nerve bundle. Compression neuropathy can occur as a result of changes in blood flow to a nerve, causing severe ischemia and consequent nerve injury (Myers, supra, 1995).

Administration of an active fragment of prosaposin according to the method of the invention also can alleviate neuropathic pain resulting from a mononeuropathy or polyneuropathy. As used herein, a neuropathy is a functional disturbance or pathological change in the peripheral nervous system and is characterized clinically by sensory or motor neuron abnormalities. The term mononeuropathy indicates that a single peripheral nerve is affected, while the term polyneuropathy indicates that several peripheral nerves are affected.

TABLE 1

Nerve

Neuroma (amputation, nerve transsection)
Nerve compression (entrapment neuropathies, tumors)
Nerve crush, stretch or incomplete transsection (trauma)
Mononeuropathy Diabetes mellitus
Irradiation
Ischemia
Vasculitis
Polyneuropathy Post-polio syndrome
Diabetes mellitus
Alcohol
Amyloid
Toxic
HIV
Hypothyroidism
Uremia
Vitamin deficiencies
Chemotherapy (vincristine, cisplatinum, paclitaxel)
ddC (zalcitabine)
Fabry's disease

TABLE 1-continued

Dorsal root ganglion

Compression (disk, tumor, scar tissue)
Root avulsion
Inflammation (postherpetic neuralgia)
Spinal cord Contusion
Tumor
Hemisection
Brainstem, thalamus, cortex
Infarction, tumors, trauma The etiology of a neuropathy can be known or unknown (see, for example, Myers, supra, 1995; Galer, *Neurology* 45(suppl 9):S17–S25 (1995); Stevens and Lowe, *Pathology*, Times Mirror International Publishers Limited, London (1995), each of which is incorporated herein by reference). Known etiologies include complications of a disease or toxic state; for example, diabetes is the most common metabolic disorder causing neuropathy. The method of the invention alleviates the neuropathic pain of a mononeuropathy resulting, for example, from diabetes, irradiation, ischemia or vasculitis. The method of the invention also alleviates the neuropathic pain of a polyneuropathy resulting, for example, from post-polio syndrome, diabetes, alcohol, amyloid, toxins, HIV, hypothyroidism, uremia, vitamin deficiencies, chemotherapy, ddC or Fabry's disease (see Table 1). The method of the invention particularly is useful in alleviating post-polio myalgia. The method of the invention also can alleviate neuropathic pain of unknown etiology.

As disclosed herein, an active fragment of prosaposin can alleviate neuropathic pain. The term "active fragment of prosaposin," as used herein, means a peptide that has an amino acid sequence corresponding to an amino acid sequence of prosaposin and that has activity in alleviating neuropathic pain. As used herein, alleviating neuropathic pain means reducing the severity of neuropathic pain. In a human subject, an active fragment of prosaposin reduces the severity of neuropathic pain such that the subject's suffering is diminished and quality of life is improved. An active fragment of prosaposin also can alleviate neuropathic pain in any one of a number of well-established animal models of neuropathic pain as described further below (also see Bennett, *Muscle & Nerve* 16:1040–1048 (1993), which is incorporated herein by reference). As used herein, the term "active fragment of prosaposin" is synonymous with "prosaposin-derived peptide".

The active fragment of prosaposin preferably contains the amino acid sequence Leu-Ile-Asp-Asn-Asn-Lys-Thr-Glu-Lys-Glu-Ile-Leu (SEQ ID NO: 3), which corresponds to amino acids 18 to 29 of saposin C. More preferably, an active fragment of prosaposin has the the amino acid sequence Cys-Glu-Phe-Leu-Val-Lys-Glu-Val-Thr-Lys-Leu-Ile-Asp-Asn-Asn-Lys-Thr-Glu-Lys-Glu-Ile-Leu (SEQ ID NO: 1), which corresponds to amino acids 8 to 29 of saposin C, or the amino acid sequence Thr-D-Ala-Leu-Ile-Asp-Asn-Asn-Ala-Thr-Glu-Glu-Ile-Leu-Tyr (SEQ ID NO: 2), which corresponds to amino acids 16 to 29 of saposin C but which has been modified by a D-alanine for lysine substitution at position 2; an alanine for lysine substitution at position 8; a deletion of lysine at position 11 and the addition of a C-terminal tyrosine residue (see Table 2). Such modifications can be useful for increasing peptide stability or uptake across the blood-brain barrier as described below. As used herein, D-alanine can be represented by D-Ala or X.

An active fragment of prosaposin can have about 12 amino acids to about 80 amino acids, which is the full-length of saposin C. Preferably, an active fragment of prosaposin has about 12 amino acids to about 40 amino acids and, more preferably, about 14 amino acids to about 22 amino acids.

TABLE 2

| PEPTIDE | SEQUENCE | SEQ ID NO: |
|---|---|---|
| Prosaposin-derived 22-mer | CEFLVKEVTKLIDNNKTEKEIL | 1 |
| Prosaposin-derived 14-mer | TXLIDNNATEEILY | 2 |
| Prosaposin-derived 12-mer | LIDNNKTEKEIL | 3 | where X = D-alanine

For use in alleviating neuropathic pain in a human subject, an active fragment of human prosaposin, such as SEQ ID NO: 1 or SEQ ID NO: 2, is preferred. However, an active fragment derived from another mammalian prosaposin also is useful in alleviating neuropathic pain according to the method of the invention. Thus, for example, an active fragment of mouse prosaposin, rat prosaposin, guinea pig prosaposin or bovine prosaposin such as SEQ ID NOS: 4 through 7 also can be useful in alleviating neuropathic pain in a subject.

The amino acid sequence of an active fragment of human prosaposin (SEQ ID NO: 1), which corresponds to amino acids 8 to 29 of saposin C, is well conserved among other species, as shown in Table 3. In particular, adjacent asparagine (N) residues are conserved among human, mouse, rat, guinea pig and bovine prosaposins. In addition, a leucine (L) residue is conserved 3 to 4 residues toward the N-terminus of the two asparagine residues and one or more charged residues (aspartic acid (D), lysine (K), glutamic acid (E) or arginine (R)) are conserved 2 to 8 residues toward the C-terminus of the two asparagine residues. Each of these well-conserved residues is underlined in Table 3.

TABLE 3

| SPECIES | SEQUENCE | SEQ ID NO. |
|---|---|---|
| Human | CEFLVKEVTK<u>L</u>ID<u>NN</u>K<u>TEKE</u>IL | 1 |
| Mouse | CQFVMNKFSE<u>L</u>IV<u>NN</u>A<u>TEE</u>LLY | 4 |
| Rat | CQLVNRKLSE<u>L</u>II<u>NN</u>A<u>TEE</u>LL- | 5 |
| Guinea Pig | CEYVVKKVML<u>L</u>ID<u>NN</u>R<u>TEEK</u>II | 6 |
| Bovine | CEFVVKEVAK<u>L</u>ID<u>NN</u>R<u>TEEE</u>IL | 7 |

The well-conserved adjacent asparagine residues, leucine residue and charged residues described above can be important for the activity of an active fragment of prosaposin in alleviating neuropathic pain. For example, the prosaposin-derived 22-mer (SEQ ID NO: 1) or the prosaposin-derived 14-mer (SEQ ID NO: 2) is an active fragment of prosaposin, which reduces the painful allodynia seen in the Chung rat model of peripheral neuropathy, as disclosed in Example I (see FIGS. 1 and 2). In contrast, a mutant 22-mer (SEQ ID NO: 8), which differs from SEQ ID NO: 1 in having an aspartic acid residue (D) in place of the first conserved asparagine (see Table 4), lacks activity in alleviating neuropathic pain as assayed using Chung rats (see Example I).

The activity of a peptide in alleviating neuropathic pain also can correlate with neurotrophic activity. For example, the prosaposin-derived 22-mer (SEQ ID NO: 1) and the prosaposin-derived 14-mer (SEQ ID NO: 2) alleviate neuropathic pain and have neurotrophic

TABLE 4

| PEPTIDE | SEQUENCE | SEQ ID NO: |
|---|---|---|
| Prosaposin-derived 22-mer | CEFLVKEVTKLIDNNKTEKEIL | 1 |
| Mutant 22-mer | CEFLVKEVTKLIDDNKTEKEIL | 8 |
| Prosaposin-derived 14-mer | TXLIDNNATEEILY | 2 |
| Mutant 14-mer M-1 | TKLIDNDKTEKEIL | 9 |
| Mutant 14-mer M-2 | TKSIDNNKTEKEIL | 10 | where X = D-alanine activity. In addition, the mutant 22-mer (SEQ ID NO: 8) is inactive in alleviating neuropathic pain as described above and lacks neurotrophic activity, further indicating that activity in alleviating neuropathic pain can correlate with neurotrophic activity. The mutant 14-mer peptide M-1 (SEQ ID NO: 9), which has a substitution of the second conserved asparagine residue, lacks neurotrophic activity, indicating that peptide SEQ ID NO: 9 also is inactive in alleviating neuropathic pain. The mutant 14-mer peptide M-2 (SEQ ID NO: 10), which has a substitution of the conserved leucine residue, lacks neurotrophic activity, indicating that peptide SEQ ID NO: 10 is inactive in alleviating neuropathic pain. In contrast, the prosaposin-derived 12-mer peptide (SEQ ID NO: 3), which has the conserved-adjacent asparagines, leucine and charged residues described above, is active as a neurotrophic factor. Thus, the prosaposin-derived 12-mer peptide (SEQ ID NO: 3) also can alleviate neuropathic pain according to the method of the invention.

A peptide useful for alleviating neuropathic pain also can be, for example, SEQ ID NOS: 11 through 19 (see Table 5). For example, sequence alignment of the prosaposin-derived 22-mer peptide SEQ ID NO: 1 with cytokines and growth factors indicates sequence similarity to a number of human (h) cytokines including hCNTF, hIL-6, hIL-2, hIL-3, hIL1-γ, erythropoietin (hEPO), human leukocyte inhibitory factor (hLIF), the hIL-1 β chain and oncostatin-M (hONC-M). SEQ ID NOS: 11 through 19, like the active fragment of prosaposin SEQ ID NO: 1, contain two asparagine residues that are adjacent or separated by one amino acid. In addition, the cytokine-derived peptide sequences can contain a leucine (L) or isoleucine (I) residue three to four residues toward the N-terminus of the two asparagine residues and one or more charged residues (aspartic acid (D), lysine (K), glutamic acid (E), or arginine (R)) two to eight residues toward the C-terminus of the two asparagine residues, as is seen in the active fragment of prosaposin (22-mer; SEQ ID NO: 1). Each of these residues is underlined in Table 5.

Models of cytokine-receptor binding (Sprang and Bazan, Curr. Opin. Struct. Biol., 3:816 (1993)) have highlighted the evolutionary conservation of a four-helical bundle structure common to many cytokines. Each of the cytokine or growth-factor sequences related to the prosaposin-derived sequence SEQ ID NO: 1 is located between helices A and B (AB loop) or within helix C of the cytokine.

TABLE 5

| CYTOKINE | SEQUENCE | LOCATION | SEQ ID NO: |
|---|---|---|---|
| Prosaposin | CEFLVKEVTKLIDNNKTEKEIL | — | 1 |
| hCNTF | YVKHQGLNKNINLDSVDGVP | AB loop | 11 |
| hIL-6 | EALAENNLNLPKMAG | AB loop | 12 |
| hIL-2 | LQMILNGINNYKNPKLT | AB loop | 13 |
| hIL-3 | ILMENNLRRPNL | AB loop | 14 |
| hIL1-γ | FYLRNNQLVAGTL | AB loop | 15 |
| hEPO | AEHCSLNENITVPDTKV | AB loop | 16 |
| hLIF | YTAQGEPFPNNVEKLCAP | AB loop | 17 |
| hIL-1β | FNKIEINNKLEFESA | Helix C | 18 |
| hONC-M | RPNILGLRNNIYCMAQLL | Helix C | 19 |

The structurally related cytokine and growth factor-dreived peptides SEQ ID NOS: 11 through 19 also can be useful in methods of alleviating neuropathic pain. Peptides SEQ ID NOS: 11 through 19 can be assayed for activity in alleviating neuropathic pain using, for example, the Chung rat model described in Example I; assays described by Wall et al., Pain 7:103–113 (1979); Bennett and Xie, Pain 33:87–107 (1988); Lekan et al., Soc. Neurosci. Abstr. 18:287 (1992) or Palacek et al., Soc. Neurosci. Abstr. 18:287 (1992), each of which is incorporated herein by reference; or other assays for neuropathic pain.

An active fragment of prosaposin or a peptide useful in alleviating neuropathic pain can be identified by screening a large collection, or library, of random peptides or peptides of interest using, for example, one of a number of animal models of neuropathic pain. Such peptides of interest can be, for example, the cytokine and growth factor-derived peptides SEQ ID NOS: 11 through 19, which have amino acid sequences related to an active fragment of prosaposin (SEQ ID NO: 1). Peptides of interest also can be, for example, a population of peptides related in amino acid sequence to SEQ ID NO: 1 by having the conserved asparagine residues, leucine/isoleucine residue and one or more charged residues at the positions corresponding to the positions in which these residues are found in SEQ ID NO: 1 but also having one or more amino acids that differ from the amino acids of SEQ ID NO: 1.

Peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid which encodes it. Methods for the production of phage display libraries, including vectors and methods of diversifying the population of peptides which are expressed, are well known in the art (see, for example, Smith and Scott, *Methods Enzymol.* 217:228–257 (1993); Scott and Smith, *Science* 249:386–390 (1990); and Huse, WO 91/07141 and WO 91/07149, each of which is incorporated herein by reference). These or other well known methods can be used to produce a phage display library, from which the displayed peptides can be cleaved and assayed for activity in alleviating neuropathic pain using, for example, one of the assays disclosed below. If desired, a population of peptides can be assayed for activity in alleviating neuropathic pain, and an active population can be subdivided and the assay repeated in order to isolate an active peptide from the population. Other methods for producing peptides useful in the invention include, for example, rational design and mutagenesis based on the amino acid sequences of active fragments of prosaposin such as SEQ ID NO: 1 and SEQ ID NO: 2, for example.

As disclosed herein, an active fragment of prosaposin or a peptide useful in alleviating neuropathic pain can be identified by its activity in alleviating neuropathic pain in any of a number of well-established animal models of neuropathic pain (Bennett, supra, 1993). For example, an active fragment of prosaposin can be identified using an experimental model of peripheral neuropathy produced by segmental spinal nerve ligation in the rat. The Chung rat model duplicates the symptoms of human patients with causalgia, or burning pain due to injury of a peripheral nerve (Kim and Chung, supra, 1992). The surgical procedure of Kim and Chung produces a long-lasting hyperalgesia to-noxious heat and mechanical allodynia of the affected foot. As described in Example I, rats with spinal nerve ligation according to the procedure developed by Chung and Kim are useful for identifying an active fragment of prosaposin for use in alleviating neuropathic pain.

An active fragment of prosaposin or a peptide useful in alleviating neuropathic pain also can be identified using the neuroma model of Wall et al. This well-recognized model of neuropathic pain reproduces the human symptoms seen following amputation or nerve transection in an intact limb (Wall et al., supra, 1979). As discussed above, a neuroma forms readily after nerve transection due to the frustrated growth of neurite sprouts.

A model of chronic constriction injury also can be used to identify an active fragment of prosaposin or a peptide useful in alleviating neuropathic pain. The chronic constriction injury model of Bennett and Xie, supra, 1988, is a rat model of peripheral neuropathy that produces pain disorders like those seen in man. In the Bennett model, nerve injury is created by loosely tying constrictive ligatures around the rat sciatic nerve, causing degeneration of nerve distal to the constriction. Allodynia and hyperalgesia are produced by the constriction injury in addition to spontaneous pain.

Primate models of neuropathic pain also are useful for identifying an active fragment of prosaposin or a peptide useful in alleviating neuropathic pain (see, for example, Lekan et al., supra, 1992; Palacek et al., supra, 1992).

As used herein, the term "peptide," as used in reference to an active fragment of prosaposin, a prosaposin-derived peptide or a peptide useful in alleviating neuropathic pain, means a compound containing naturally occurring amino acids, non-naturally occurring amino acids or chemically modified amino acids, provided that the compound retains activity in alleviating neuropathic pain. A prosaposin-derived peptide also can be a peptide mimetic, which is a non-amino acid chemical structure that mimics the structure of a prosaposin-derived peptide and retains activity in alleviating neuropathic pain. Such a mimetic generally is characterized as exhibiting similar physical characteristics such as size, charge or hydrophobicity in the same spatial arrangement found in the prosaposin-derived peptide counterpart. A specific example of a peptide mimetic is a compound in which the amide bond between one or more of the amino acids is replaced, for example, by a carbon-carbon bond or other bond well known in the art (see, for example, Sawyer, *Peptide Based Drua Design*, ACS, Washington (1995), which is incorporated herein by reference).

As used herein, the term "amino acid" refers to one of the twenty naturally occurring amino acids, including, unless stated otherwise, L-amino acids and D-amino acids. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains its biological activity. For example, glutamine can be an amino acid analog of asparagine, provided that it can be substituted within an active fragment of prosaposin that retains its activity in alleviating neuropathic pain. Other examples of amino acids and amino acids analogs are listed in Gross and Meienhofer, *The Peptides: Analysis. Synthesis, Biology*, Academic Press, Inc., New York (1983), which is incorporated herein by reference. An amino acid also can be an amino acid mimetic, which is a structure that exhibits substantially the same spatial arrangement of functional groups as an amino acid but does not necessarily have both the $\alpha$-amino and $\alpha$-carboxyl groups characteristic of an amino acid.

An active fragment of prosaposin or a peptide useful in the invention can be isolated or synthesized using methods well known in the art. Such methods include recombinant DNA methods and chemical synthesis methods for production of a peptide. Recombinant methods of producing a peptide through expression of a nucleic acid sequence encoding the peptide in a suitable host cell are well known in the art and are described, for example, in Sambrook et al., *Molecular Cloning: A Laboratory Manual*, 2nd Ed, Vols 1 to 3, Cold Spring Harbor Laboratory Press, New York (1989), which is incorporated herein by reference.

An active fragment of prosaposin or a peptide useful in the invention also can be produced by chemical synthesis, for example, by the solid phase peptide synthesis method of Merrifield et al., *J. Am. Chem. Soc.* 85:2149 (1964), which is incorporated herein by reference. Standard solution methods well known in the art also can be used to synthesize a peptide useful in the invention (see, for example, Bodanszky, *Principles of Peptide Synthesis*, Springer-Verlag, Berlin (1984) and Bodanszky, *Peptide Chemistry*, Springer-Verlag, Berlin (1993), each of which is incorporated herein by reference). A newly synthesized peptide can be purified, for example, by high performance liquid chromatography (HPLC), and can be characterized using, for example, mass spectrometry or amino acid sequence analysis.

It is understood that limited modifications can be made to an active fragment of prosaposin without destroying its biological function. Thus, a modification of an active fragment of prosaposin that does not destroy its ability to alleviate neuropathic pain is within the definition of an active fragment of prosaposin. A modification can include, for example, an addition, deletion, or substitution of amino acid residues; a substitution of a compound that mimics amino acid structure or function; and addition of chemical moieties such as amino or acetyl groups. The activity of a modified peptide in alleviating neuropathic pain can be assayed using an animal model of neuropathic pain, such as those described above or the assay exemplified in Example I.

A particularly useful modification of an active fragment of prosaposin is one that confers, for example, increased stability. For example, incorporation of one or more D-amino acids or substitution or deletion of lysine can increase the stability of an active fragment of prosaposin by protecting against peptide degradation. For example, as disclosed herein, the prosaposin-derived 14-mer SEQ ID NO: 2 has an amino acid sequence derived from amino acids 16 to 29 of saposin C but which has been modified by substitution or deletion of each of the three naturally occurring lysines and the addition of a C-terminal tyrosine residue. In particular, the prosaposin-derived 14-mer SEQ ID NO: 2 has a D-alanine for lysine substitution at position 2; an alanine for lysine substitution at position 8 and a deletion of lysine at position 11. The D-alanine substitution at position 2 confers increased stability by protecting the peptide from endoprotease degradation, as is well known in the art (see, for example, page 247 of Partridge, *Peptide Drug Delivery to the Brain*, Raven Press, New York (1991), which is incorporated herein by reference). The substitution or deletion of a lysine residue confers increased resistance to trypsin-like proteases, as is well known in the art (Partridge, supra, 1991). These substitutions increase stability and, thus, bioavailability of peptide SEQ ID NO: 2, but do not affect activity in alleviating neuropathic pain.

A useful modification also can be one that promotes peptide passage across the blood-brain barrier, such as a modification that increases lipophilicity or decreases hydrogen bonding. For example, a tyrosine residue added to the C-terminus of the prosaposin-derived peptide (SEQ ID NO: 2) increases hydrophobicity and permeability to the blood-brain barrier (see, for example, Banks et al., *Peptides* 13:1289–1294 (1992, which is incorporated herein by reference, and Pardridge, supra, 1991). A chimeric peptide-pharmaceutical that has increased biological stability or increased permeability to the blood-brain barrier, for example, also can be useful in the method of the invention.

One skilled in the art can readily assay the ability of an active fragment of prosaposin to cross the blood-brain barrier in vivo, for example, as disclosed in Example II. In addition, an active fragment of prosaposin can be tested for its ability to cross the blood-brain barrier using an in vitro model of the blood-brain barrier based on a brain microvessel endothelial cell culture system, for example as described in Bowman et al., *Ann. Neurol.* 14:396–402 (1983) or Takahura et al., *Adv. Pharmacol.* 22:137–165 (1992), each of which is incorporated herein by reference.

As used herein, the term "effective amount" means the amount of an active fragment of prosaposin useful for alleviating neuropathic pain or for preventing neuropathic pain. An effective amount to be administered systemically on a daily basis depends on the body weight of the subject. Preferably, an-effective amount to be administered systemically on a daily basis is about 0.1 $\mu$g/kg to about 1000 $\mu$g/kg. More preferably, an effective amount to be administered systemically on a daily basis is about 10 $\mu$g/kg to about 100 $\mu$g/kg. An effective amount of a peptide for alleviating or preventing pain can be determined empirically using methods well known to those in the art, including, for example, the assay described in Example I or those disclosed above, including assays in primates (Lekan et al., supra, 1992, and Palacek et al., supra, 1992).

As used herein, the term "subject" means a vertebrate, preferably a mammal and, in particular, a human.

The present invention provides a method of alleviating pain by administering an effective amount of an active fragment of prosaposin intravenously, intramuscularly, intradermally, subcutaneously, intracranially, intracerebrospinally, topically or orally. A pharmaceutically acceptable carrier of well known type can be administered with an active fragment of prosaposin. Such carriers include, for example, phosphate buffered saline (PBS).

Preferably, an effective amount of an active fragment of prosaposin is injected directly into the bloodstream of the subject. For example, intravenous injection of an active fragment of prosaposin can be used to administer the active fragment to the peripheral or central nervous system, since an iodinated prosaposin-derived 18-mer Tyr-Lys-Glu-Val-Thr-Lys-Leu-Ile-Asp-Asn-Asn-Lys-Thr-Glu-Lys-Glu-Ile-Leu (SEQ ID NO: 20), consisting of amino acids 12 to 29 of prosaposin-derived 22-mer SEQ ID NO: 1 with a substitution of tyrosine for valine at amino acid 12 (MW=2000) crossed the blood-brain barrier and entered the central nervous system as described in Example II. The uptake by the brain was approximately 0.03%, which is in the midrange of values for peptides of that approximate size that will cross the blood-brain barrier (Banks et al., supra, 1992).

Oral administration often can be desirable, provided the active fragment of prosaposin is modified so as to be stable to gastrointestinal degradation and readily absorbable. The substitution, for example, of one or more D-amino acids can confer increased stability to a prosaposin-derived peptide useful in the invention.

Direct intracranial injection or injection into the cerebrospinal fluid also can be used to introduce an effective amount of an active fragment of prosaposin into the central nervous system of a subject. In addition, an active fragment of prosaposin can be administered to peripheral neural tissue by direct injection or local topical application or by systemic administration. Various conventional modes of administration also are contemplated, including intravenous, intramuscular, intradermal, subcutaneous, intracranial, epidural, topical and oral administration.

An active fragment of prosaposin also can be administered in a sustained release form. The sustained release of an active fragment of prosaposin has the advantage of alleviating neuropathic pain over an extended period of time without the need for repeated administrations of the active fragment.

Sustained release can be achieved, for example, with a sustained release material such as a wafer, an immunobead, a micropump or other material that provides for controlled slow release of the active fragment of prosaposin. Such controlled release materials are well known in the art and available from commercial sources (Alza Corp., Palo Alto Calif.; Depotech, La Jolla Calif.; see, also, Pardoll, *Ann. Rev. Immunol.* 13:399–415 (1995), which is incorporated herein by reference). In addition, a bioerodible or biodegradable material that can be formulated with an active fragment of prosaposin, such as polylactic acid, polygalactic acid, regenerated collagen, multilamellar liposomes or other conventional depot formulations, can be implanted to slowly release the active fragment of prosaposin. The use of infusion pumps, matrix entrapment systems, and transdermal delivery devices also are contemplated in the present invention.

An active fragment of prosaposin also can be advantageously enclosed in micelles or liposomes. Liposome encapsulation technology is well known. Liposomes can be targeted to a specific tissue, such as neural tissue, through the use of receptors, ligands or antibodies capable of binding the targeted tissue. The preparation of these formulations is well known in the art (see, for example, Pardridge, supra, 1991, and Radin and Metz, *Meth. Enzymol.* 98:613–618 (1983), which is incorporated herein by reference).

The invention also provides a method of alleviating neuropathic pain in a subject by transplanting into the subject a cell genetically modified to express and secrete an active fragment of prosaposin. Transplantation can provide a continuous source of an active fragment of prosaposin and, thus, sustained alleviation of neuropathic pain. For a subject suffering from prolonged or chronic neuropathic pain, such a method has the advantage of obviating or reducing the need for repeated administration of an active fragment of prosaposin.

Using methods well known in the art, a cell readily can be transfected with an expression vector containing a nucleic acid encoding an active fragment of prosaposin (Chang, *Somatic Gene Therapy*, CRC Press, Boca Raton (1995), which is incorporated herein by reference). Following transplantation into the brain, for example, the transfected cell expresses and secretes an active fragment of prosaposin and, thus, alleviates neuropathic pain. Such a method can be useful to alleviate neuropathic pain as described for the transplantation of cells that secrete substances with analgesic properties (see, for example, Czech and Sagen, *Prog. Neurobiol.* 46:507–529 (1995), which is incorporated herein by reference).

The cell can be any cell that can survive when transplanted and that can be modified to express and secrete an active fragment of prosaposin. In practice, the cell should be immunologically compatible with the subject. For example, a particularly useful cell is a cell isolated from the subject to be treated, since such a cell is immunologically compatible with the subject.

A cell derived from a source other than the subject to be treated also can be useful if protected from immune rejection using, for example, microencapsulation or immunosuppression. Useful microencapsulation membrane materials include alginate-poly-L-lysine alginate and agarose (see, for example, Goosen, *Fundamentals of Animal Cell Encapsulation and Immobilization*, CRC Press, Boca Raton (1993); Tai and Sun, *FASEB J.* 7:1061 (1993); Liu et al., *Hum. Gene Ther.* 4:291 (1993); and Taniguchi et al., *Transplant. Proc.* 24:2977 (1992), each of which is incorporated herein by reference). For example, pain reduction has been achieved using polymer encapsulated cells transplanted into the rat spinal subarachnoid space (Wang et al., *Soc. Neurosci. Abstr.* 17:235 (1991), which is incorporated herein by reference).

For treatment of a human subject, the cell can be a human cell, although a non-human mammalian cell also can be useful. In particular, a human fibroblast, muscle cell, glial cell, neuronal precursor cell or neuron can be transfected with an expression vector to express and secrete an active fragment of prosaposin such as SEQ ID NO: 1. A primary fibroblast can be obtained, for example, from a skin biopsy of the subject to be treated and maintained under standard tissue culture conditions. A primary muscle cell also can be useful for transplantation. Considerations for neural transplantation are described, for example, in Chang, supra, 1995.

A cell derived from the central nervous system can be particularly useful for transplantation to the central nervous system since the survival of such a cell is enhanced within its natural environment. A neuronal precursor cell is particularly useful in the method of the invention since a neuronal precursor cell can be grown in culture, transfected with an expression vector and introduced into an individual, where it is integrated. The isolation of neuronal precursor cells, which are capable of proliferating and differentiating into neurons and glial cells, is described in Renfranz et al., *Cell* 66:713–729 (1991), which is incorporated herein by reference.

Methods of transfecting cells ex vivo are well known in the art (Kriegler, *Gene Transfer and Expression: A Laboratory Manual*, W.H. Freeman & Co., New York (1990)). For the transfection of a cell that continues to divide such as a fibroblast, muscle cell, glial cell or neuronal precursor cell, a retroviral vector is preferred. For the transfection of an expression vector into a postmitotic cell such as a neuron, a replication-defective herpes simplex virus type 1 (HSV-1) vector is useful (During et al., *Soc. Neurosci. Abstr.* 17:140 (1991); Sable et al., *Soc. Neurosci. Abstr.* 17:570 (1991), each of which is incorporated herein by reference).

A nucleic acid encoding an active fragment of prosaposin can be expressed under the control of one of a variety of promoters well known in the art, including a constitutive promoter or inducible promoter. See, for example, Chang, supra, 1995. A particularly useful constitutive promoter for high level expression is the Moloney murine leukemia virus long-terminal repeat (MLV-LTR), the cytomegalovirus immediate-early (CMV-IE) or the simian virus 40 early region (SV40).

A nucleic acid sequence encoding an active fragment of prosaposin is disclosed herein. For example, a nucleic acid sequence encoding SEQ ID NO: 1 is 5'-TGTGAATTCCTGGTGAAGGAGGTGACCAAGCT GATTGACAACAACAAGACTGAG AAAGAAATACTC-3' (SEQ ID NO: 21) (Dewji et al., *Proc. Natl. Acad. Sci. USA* 84:8652–8656 (1987), which is incorporated herein by reference). In order to direct secretion of peptide SEQ ID NO: 1, for example, a nucleic acid encoding a signal sequence, such as the signal sequence of β-lactamase, can be operably linked to SEQ ID NO: 21 as described in Simon et al., *J. Cell Biol.* 104:1165 (1987), which is incorporated herein by reference.

The invention further provides a method of preventing neuropathic pain in a subject by administering an effective amount of an active fragment of prosaposin to the subject. The method of preventing neuropathic pain is useful when applied prior to a painful event, for example, prior to chemotherapy or surgery that is known to result in neuropathic pain.

The following examples are intended to illustrate but not limit the present invention.

EXAMPLE I

Alleviation of Neuropathic Pain in Chung Model Rats

This example describes the effects of bolus intrathecal injection of an active fragment of prosaposin in the Chung experimental model of peripheral neuropathic pain.

Each of the three peptides were obtained in pure form by chemical synthesis, dissolved in sterile PBS and buffered to a neutral pH.

The surgical procedure previously described by Kim and Chung, supra, 1992, was performed on male Sprague-Dawley rats weighing 120 to 150 grams to induce an allodynic state. Briefly, the rats were anesthetized with halothane; subsequently, the left L-5 and L-6 spinal nerves were isolated adjacent to the vertebral column and ligated with 6.0 silk suture distal to the dorsal root ganglion. After a ten to fourteen day post operative recovery period, a spinal catheter was introduced. Five days following the second surgery, intrathecal drug administration was accomplished using a gear driven micro-injection syringe connected to a spinal catheter inserted through the foramen magnum. Prior to testing, the rats were placed in clear plastic wire meshed cages and allowed to accommodate.

To assess the 50% mechanical threshold for paw withdrawal, a von Frey hair was applied to the hind foot avoiding the foot pad. Each of the von Frey hairs, which are calibrated to bend at increasing log forces, were pressed perpendicularly to the foot with sufficient force to cause slight bending for a duration of approximately six to eight seconds. A positive response was noted if the foot was sharply withdrawn. Six data points were collected for each point with the maximum and minimum stimulus noted for each time point. The resulting pattern of the responses was tabulated, and the 50% response threshold was computed. The graph gives the response to the indicated dosage of peptide given as a single intrathecal bolus injection. The X-axis indicates the time after the injection at which point the hypersensitivity to pressure on the foot pad was measured.

All surgically lesioned rats showed tactile allodynia prior to injection with an active fragment of prosaposin. As shown at time zero in FIG. 1, the measured threshold was less than 3.0 to 4.0 g in the absence of peptide. Intrathecal injection of 0.7 or 0.07 μg of the prosaposin-derived 22-mer peptide (SEQ ID NO: 1) suppressed allodynia in a dose-dependent fashion. The reduction of allodynia is manifest by the increase in the force threshold as the rats withstand an increasing force before withdrawing the affected foot.

A significant effect was observed by 15 minutes after the injection. The maximum effect was seen 120 minutes post-injection. Rats injected with the highest dose of the prosaposin-derived 22-mer peptide (SEQ ID NO: 1) continued to demonstrate significantly reduced allodynia at the latest time point assayed (180 minutes) Rats that were injected with 0.007 μg prosaposin-derived 22-mer peptide (SEQ ID NO: 1) showed no significant reduction in allodynia. No significant side effects such as sedation were observed at any concentration.

Figure 2:
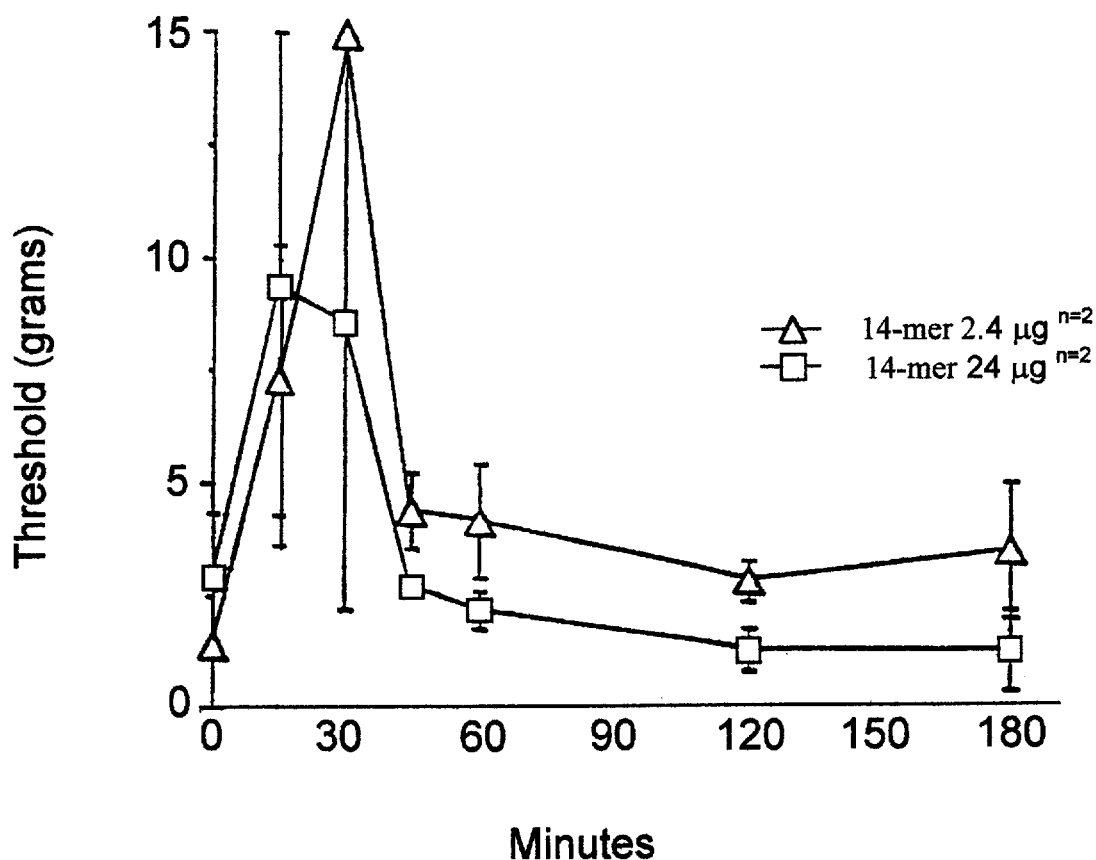
FIG. 2 shows the threshold of tactile allodynia before (time 0) and at various times after bolus injection of prosaposin-derived 14-mer peptide (SEQ ID NO: 2) in Chung model rats.

The ability of the prosaposin-derived 14-mer peptide (SEQ ID NO: 2; see Table 1) to relieve allodynia in Chung model rats also was examined. As shown in FIG. 2, the active fragment of prosaposin (SEQ ID NO: 2) was effective in reducing allodynia. The peak effect of the prosaposin-derived 14-mer peptide (SEQ ID NO: 2) was observed 15 to 30 minutes following the injection and returned to the pre-injection value by 60 minutes (FIG. 2). No side effects were observed at either concentration of prosaposin-derived 14-mer peptide (SEQ ID NO: 2) tested.

A mutant 22-mer peptide (SEQ ID NO: 8) that differs from the prosaposin-derived 22-mer peptide (SEQ ID NO: 1) by containing an aspartic acid residue instead of an asparagine (see Table 4) also was tested for activity in relieving allodynia in Chung model rats. No change in the allodynic response of the Chung rats was observed following injection of 17.5 μg mutant 22-mer peptide (SEQ ID NO: 8).

Normal rats, which do not experience pain as a result of surgical lesion introduced according to the Chung model, also were injected with an active fragment of prosaposin (SEQ ID NO: 1) and tested for their response to a heat stimulus according to the procedure developed by Bennett and Xie, supra, 1988. Briefly, the period of time before the rat withdraws the affected foot from a source of heat is defined as the hot plate latency and is a measure of tolerance to pain caused by a heat stimulus.

An intrathecal catheter was placed into normal male Sprague Dawley rats. Five days after this surgery, rats were injected intrathecally with an active fragment of prosaposin (SEQ ID NO: 1). Rats were examined on the hot plate (52.5° C.); hot plate response latencies were measured prior to injection and at various time points up to 180 minutes after the injection. No significant elevation of the hot plate response latency was observed. Thus, the prosaposin-derived peptide SEQ ID NO: 1 does not effect the perception of pain in normal animals.

EXAMPLE II

In vivo Uptake of Prosaposin-derived Peptide by the Central Nervous System

An 18-mer peptide (SEQ ID NO: 20) consisting of amino acids 12–29 of saposin C with a tyrosine substituted for valine at position 12 was chemically synthesized on an Applied Biosystems Model 430 peptide synthesizer. The peptide was then radioiodinated by the lactoperoxidase method; $20 \times 10^6$ cpm radiolabeled peptide were injected into the auricles of rats. The animals were sacrificed after one hour and 24 hours, and the hearts were perfused with isotonic saline in order to remove the blood from the brain.

In order to determine the percentage of peptide uptake, the brain was then counted in a gamma counter. In addition, the brain was homogenized and fractionated into a capillary rich fraction (pellet) and a parenchymal brain fraction (supernatant) after dextran centrifugation (Triguero et al., *J. Neurochem.*, 54:1882–1888 (1990), which is incorporated herein by reference). This method allows for the discrimination between radiolabeled peptide within blood vessels and that within the brain. After 24 hours, 0.017% of the injected peptide (SEQ ID NO: 20) was detected in whole brain; 75% of the label was in the parenchymal fraction and 25% was in the capillary fraction. At 1 hour, 0.03% of the injected dose was present in whole brain.

Although the invention has been described with reference to the examples above, it should be understood that various modifications can be made without departing from the spirit of the invention. Accordingly, the invention is limited only by the following claims.

What is claimed is:

1. A method for treating prosaposin-responsive neuropathic pain of the peripheral nervous system, comprising administering to a subject suffering from prosaposin-responsive neuropathic pain an effective amount of an active fragment of prosaposin comprising the active fragment located within SEQ ID NO:1;

wherein the subject's perceived neuropathic pain is eliminated or reduced.

2. The method of claim 1, wherein said active fragment of prosaposin consists of SEQ ID NO:1.

3. The method of claim 1, wherein said administering is by a route selected from the group consisting of intravenous, intramuscular, intradermal, subcutaneous, topical, and oral.

4. The method of claim 1, wherein said active fragment of prosaposin consists of an amino acid sequence as set forth in SEQ ID NO:3.

5. The method of claim 1, wherein said prosaposin-responsive neuropathic pain is characterized by hyperalgesia.

6. A method for treating prosaposin-responsive neuropathic pain of the peripheral nervous system, comprising administering to a subject suffering from prosaposin-responsive neuropathic pain, an effective amount of a polypeptide comprising an amino acid sequence selected from the group consisting of SEQ ID NO:2, SEQ ID NO:4, SEQ ID NO:5, SEQ ID NO:6, and SEQ ID NO:7 wherein the subject's perceived neuropathic pain is eliminated or reduced.

7. The method of claim 6, wherein said polypeptide consists of an amino acid sequence selected from the group consisting of SEQ ID NO:2, SEQ ID NO:4, SEQ ID NO:5, SEQ ID NO:6, and SEQ ID NO:7.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:1:

Cys Glu Phe Leu Val Lys Glu Val Thr Lys Leu Ile Asp Asn Asn Lys
1               5                   10                  15

Thr Glu Lys Glu Ile Leu
            20

(2) INFORMATION FOR SEQ ID NO:2:

(i) SEQUENCE CHARACTERISTICS:
        (A) LENGTH: 14 amino acids
        (B) TYPE: amino acid
        (D) TOPOLOGY: linear (ix) FEATURE:
        (A) NAME/KEY: Peptide
        (B) LOCATION: 2
        (D) OTHER INFORMATION: /note= "Xaa is D-alanine"

(xi) SEQUENCE DESCRIPTION: SEQ ID NO:2:

Thr Xaa Leu Ile Asp Asn Asn Ala Thr Glu Glu Ile Leu Tyr
1               5                   10

(2) INFORMATION FOR SEQ ID NO:3:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:3:

Leu Ile Asp Asn Asn Lys Thr Glu Lys Glu Ile Leu
1               5                   10

(2) INFORMATION FOR SEQ ID NO:4:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:4:

Cys Gln Phe Val Met Asn Lys Phe Ser Glu Leu Ile Val Asn Asn Ala
1               5                   10                  15

Thr Glu Glu Leu Leu Tyr
            20

(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO:5:

```
Cys Gln Leu Val Asn Arg Lys Leu Ser Glu Leu Ile Ile Asn Asn Ala
1               5                   10                  15

Thr Glu Glu Leu Leu
            20
```

(2) INFORMATION FOR SEQ ID NO:6:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:6:

```
Cys Glu Tyr Val Val Lys Lys Val Met Leu Leu Ile Asp Asn Asn Arg
1               5                   10                  15

Thr Glu Glu Lys Ile Ile
            20
```

(2) INFORMATION FOR SEQ ID NO:7:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:7:

```
Cys Glu Phe Val Val Lys Glu Val Ala Lys Leu Ile Asp Asn Asn Arg
1               5                   10                  15

Thr Glu Glu Glu Ile Leu
            20
```

(2) INFORMATION FOR SEQ ID NO:8:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:8:

```
Cys Glu Phe Leu Val Lys Glu Val Thr Lys Leu Ile Asp Asp Asn Lys
1               5                   10                  15

Thr Glu Lys Glu Ile Leu
            20
```

(2) INFORMATION FOR SEQ ID NO:9:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:9:

```
Thr Lys Leu Ile Asp Asn Asp Lys Thr Glu Lys Glu Ile Leu
1               5                   10
```

(2) INFORMATION FOR SEQ ID NO:10:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:10:

```
Thr Lys Ser Ile Asp Asn Asn Lys Thr Glu Lys Glu Ile Leu
```

```
1               5                  10
```

(2) INFORMATION FOR SEQ ID NO:11:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO:11:

```
Tyr Val Lys His Gln Gly Leu Asn Lys Asn Ile Asn Leu Asp Ser Val
1               5                  10                  15

Asp Gly Val Pro
            20
```

(2) INFORMATION FOR SEQ ID NO:12:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:12:

```
Glu Ala Leu Ala Glu Asn Asn Leu Asn Leu Pro Lys Met Ala Gly
1               5                  10                  15
```

(2) INFORMATION FOR SEQ ID NO:13:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:13:

```
Leu Gln Met Ile Leu Asn Gly Ile Asn Asn Tyr Lys Asn Pro Lys Leu
1               5                  10                  15

Thr
```

(2) INFORMATION FOR SEQ ID NO:14:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:14:

```
Ile Leu Met Glu Asn Asn Leu Arg Arg Pro Asn Leu
1               5                  10
```

(2) INFORMATION FOR SEQ ID NO:15:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:15:

```
Phe Tyr Leu Arg Asn Asn Gln Leu Val Ala Gly Thr Leu
1               5                  10
```

(2) INFORMATION FOR SEQ ID NO:16:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO:16:

Ala Glu His Cys Ser Leu Asn Glu Asn Ile Thr Val Pro Asp Thr Lys
1               5                   10                  15
Val (2) INFORMATION FOR SEQ ID NO:17:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:17:

Tyr Thr Ala Gln Gly Glu Pro Phe Pro Asn Asn Val Glu Lys Leu Cys
1               5                   10                  15
Ala Pro (2) INFORMATION FOR SEQ ID NO:18:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:18:

Phe Asn Lys Ile Glu Ile Asn Asn Lys Leu Glu Phe Glu Ser Ala
1               5                   10                  15

(2) INFORMATION FOR SEQ ID NO:19:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:19:

Arg Pro Asn Ile Leu Gly Leu Arg Asn Asn Ile Tyr Cys Met Ala Gln
1               5                   10                  15
Leu Leu (2) INFORMATION FOR SEQ ID NO:20:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:20:

Tyr Lys Glu Val Thr Lys Leu Ile Asp Asn Asn Lys Thr Glu Lys Glu
1               5                   10                  15
Ile Leu (2) INFORMATION FOR SEQ ID NO:21:

(i) SEQUENCE CHARACTERISTICS:
        (A) LENGTH: 66 base pairs
        (B) TYPE: nucleic acid
        (C) STRANDEDNESS: double
        (D) TOPOLOGY: linear -continued (xi) SEQUENCE DESCRIPTION: SEQ ID NO:21:

```
TGTGAATTCC TGGTGAAGGA GGTGACCAAG CTGATTGACA ACAACAAGAC TGAGAAAGAA        60
ATACTC                                                                  66
```